US008092384B2

(12) United States Patent
Meyer

(10) Patent No.: US 8,092,384 B2
(45) Date of Patent: Jan. 10, 2012

(54) SYSTEM AND METHOD FOR CONTINUOUS DETECTION OF AN ANALYTE IN BLOODSTREAM

(75) Inventor: Peter Meyer, Shrewsbury, MA (US)

(73) Assignee: Tyco Healthcare Group LP, Mansfield, MA (US)

( * ) Notice: Subject to any disclaimer, the term of this patent is extended or adjusted under 35 U.S.C. 154(b) by 1504 days.

(21) Appl. No.: 11/528,907

(22) Filed: Sep. 28, 2006

(65) Prior Publication Data

US 2008/0086037 A1 Apr. 10, 2008

(51) Int. Cl.
- *A61B 5/145* (2006.01)
- *G01N 33/48* (2006.01)
- *G01N 15/06* (2006.01)
- *C12Q 1/00* (2006.01)

(52) U.S. Cl. .............. 600/309; 702/19; 422/68.1; 435/4

(58) Field of Classification Search .................. 600/309, 600/459, 437; 435/6, 7.1, 4; 436/501; 422/68.1; 702/19; 73/64.53

See application file for complete search history.

(56) References Cited

U.S. PATENT DOCUMENTS

| | | | |
|---|---|---|---|
| 4,999,284 A | | 3/1991 | Ward et al. |
| 5,000,185 A * | | 3/1991 | Yock .............................. 600/459 |
| 5,139,328 A | | 8/1992 | Baker et al. |
| 5,421,328 A * | | 6/1995 | Bedingham .................... 600/309 |
| 5,501,986 A | | 3/1996 | Ward et al. |
| 5,503,982 A | | 4/1996 | Hendricks et al. |
| 5,658,732 A * | | 8/1997 | Ebersole et al. ................... 435/6 |
| 5,705,399 A * | | 1/1998 | Larue ............................ 436/501 |
| 5,730,144 A | | 3/1998 | Katz et al. |
| 5,795,725 A * | | 8/1998 | Buechler et al. ............... 435/7.1 |
| 5,814,525 A | | 9/1998 | Renschler et al. |
| 6,200,532 B1 | | 3/2001 | Wu et al. |
| 6,486,588 B2 | | 11/2002 | Doron et al. |
| 6,692,437 B2 | | 2/2004 | Kensey et al. |
| 6,709,390 B1 | | 3/2004 | Marie Pop |
| 6,848,295 B2 | | 2/2005 | Auner et al. |
| 7,111,500 B2 * | | 9/2006 | Itoh et al. ...................... 73/54.41 |
| 2003/0009093 A1 | | 1/2003 | Silver |
| 2005/0015001 A1 | | 1/2005 | Lee et al. |
| 2005/0215871 A1 * | | 9/2005 | Feldman et al. ............... 600/309 |
| 2006/0057635 A1 * | | 3/2006 | Mansson et al. ............... 435/7.1 |

* cited by examiner

*Primary Examiner* — Eric Winakur
*Assistant Examiner* — Chu Chuan (JJ) Liu
(74) *Attorney, Agent, or Firm* — Thomas M. Johnston, Esq.

(57) ABSTRACT

A method for performing a blood assay is disclosed. The method includes the steps of: positioning an acoustic biosensor in fluid communication with a blood vessel of the patient whereby blood from the blood vessel contacts the biosensor. The biosensor includes at least one material adapted to bind to an analyte. The method also includes the steps of detecting a change in at least one of an electrical and mechanical property of the biosensor indicative of a mass change resulting from binding of the at least one material with the analyte and transmitting a real time signal representative of mass change to a display module to provide real time analysis by a clinician.

25 Claims, 4 Drawing Sheets

SYSTEM AND METHOD FOR CONTINUOUS DETECTION OF AN ANALYTE IN BLOODSTREAM

BACKGROUND

1. Technical Field

The present disclosure relates to a system and method for performing blood assays. In particular, the present disclosure is directed to in vivo acoustic biosensors configured to continuously monitor blood to detect presence and/or concentration of an analyte of interest.

2. Background of Related Art

Various types of blood analyzers for detecting specific analytes of interest (e.g., proteins) are known in the art. A conventional blood analyzer utilizes a sensor to detect the presence of the analyte and optionally determines the concentration thereof. In vitro methods are usually utilized to obtain a blood sample from a blood vessel and subsequently provide the sample to the blood analyzer for analysis.

However, known blood analyzers of the type aforementioned present a major drawback which detracts from their overall usefulness and effectiveness. In particular, the conventional blood analyzer is incapable of providing real or present time data of the analyte of interest present in the blood stream. Moreover, the conventional blood analyzer is limited in that it can only indicate the presence of the analyte at the moment when the sample of blood was drawn. In many applications, the amount of analyte present does not exhibit elevated concentrations in the bloodstream until several hours after the biological event.

One conventional solution involves performing multiple in vitro assays to periodically screen the blood for elevated concentration of the analyte. However, performing multiple assays is overly invasive to the patient. In addition, this solution is also imperfect since there is a possibility that occurrence of the biological event may be missed.

This particular problem is acutely prevalent in the field of monitoring of acute myocardial infarction patients. Biochemical markers associated with myocardial infarction (e.g., cardiac troponin) are detectable in the patient's blood stream about 3 to 8 hours from the onset of the condition. In the absence of other indications of the condition (e.g., electrocardiogram indicators, acute distress, etc.) a patient complaining of physical conditions associated with myocardial infarction (e.g., chest pain) is typically observed for up to 12 hours to rule out the infarction as the cause of the symptoms. Conventionally, cardiac marker assays are typically performed serially at 6-8 hour intervals in order to detect a recent infarction. Due to the relatively long time periods between assays, a true infarction patient with biological signs of infarction may, as a result, wait for many hours before the signs are detected. Consequently, there is a delay in providing therapy to the patient.

Therefore it would be desirable to provide a blood analyzer that continuously detects the presence of an analyte in a bloodstream to allow for instantaneous and continuous detection of elevated analyte concentration.

SUMMARY

The present disclosure relates to a system and method for performing in vivo blood assay to detect the presence and concentration of an analyte. The system includes an acoustic biosensor having an antibody material adapted to bind to the analyte of interest. The biosensor is in fluid communication with a blood vessel such that blood continuously contacts the biosensor and the analyte binds to the antibody material. The biosensor is repeatedly excited and the biosensor's resonant frequency is repeatedly monitored, therefore approximating a continuous measurement. Changes in the resonant frequency are recorded and analyzed by a detector device which calculates the concentration of the analyte in the bloodstream.

According to one aspect of the present disclosure a method for performing a blood assay is disclosed. The method includes the steps of: positioning an acoustic biosensor in fluid communication with a blood vessel of the patient whereby blood from the blood vessel contacts the biosensor. The biosensor includes at least one material adapted to bind to an analyte. The method also includes the steps of detecting a change in at least one of an electrical and mechanical property of the biosensor indicative of a mass change resulting from binding of the at least one material with the analyte and transmitting a real time signal representative of mass change to a display module to provide real time analysis by a clinician.

According to another aspect of the present disclosure a medical analyzer to assay blood for an analyte is disclosed. The analyzer includes an acoustic biosensor adapted to be in fluid communication with a blood vessel whereby blood from the blood vessel contacts the biosensor. The biosensor includes at least one material adapted to bind to an analyte in the blood. The analyzer also includes an oscillator for generating a mechanical wave form in the biosensor and a detector adapted to detect a change in resonant frequency of the mechanical wave form indicative of a mass change resulting from the binding of the at least one material of the biosensor with the analyte of the blood. The detector is also adapted to generate a real time signal representative of the mass change of the biosensor to provide real time analysis by a clinician.

According to an additional embodiment of the present disclosure, a medical analyzer to assay blood for an analyte is disclosed. The medical analyzer includes an acoustic biosensor adapted to be in fluid communication with a blood vessel whereby blood from the blood vessel contacts the biosensor. The biosensor includes at least one material adapted to bind to an analyte of the blood and is adapted to transmit a mass change resulting from the binding of the at least one material of the biosensor with the analyte of the blood in response to a change in at least one of an electrical and mechanical property of the biosensor.

BRIEF DESCRIPTION OF THE DRAWINGS

Various embodiments of the present disclosure are described herein with reference to the drawings wherein.

DETAILED DESCRIPTION

Particular embodiments of the present disclosure are described hereinbelow with reference to the accompanying drawings. In the following description, well-known functions or constructions are not described in detail to avoid obscuring the present disclosure in unnecessary detail.

Figure 1:
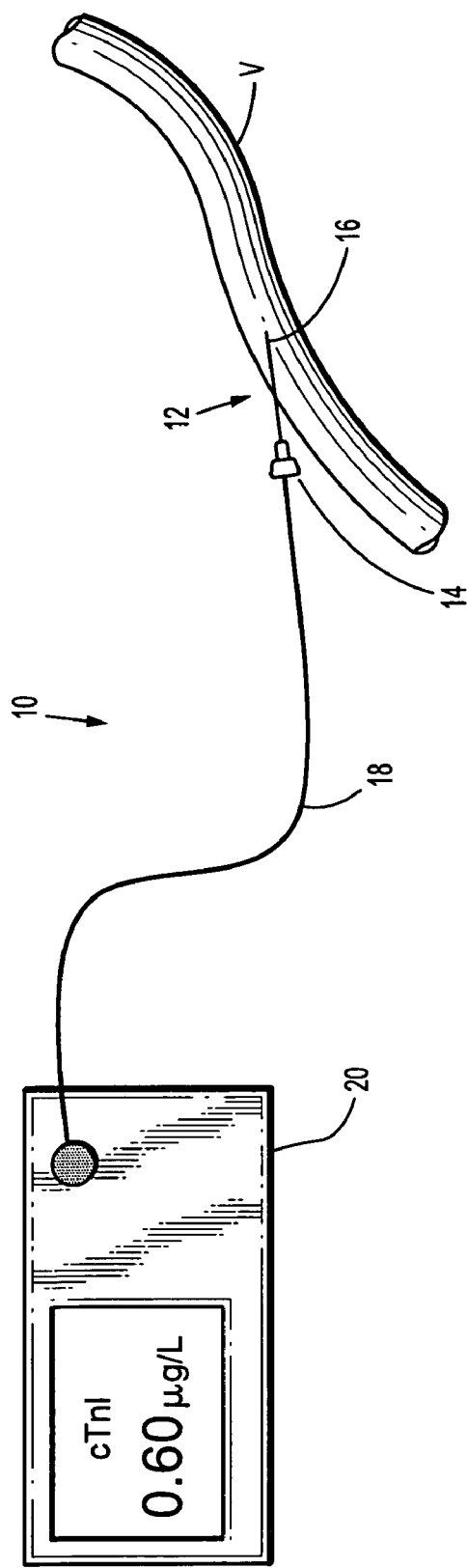
FIG. 1 is a view of a blood analyzer according to the present disclosure accessing a blood vessel.
Figure 2:
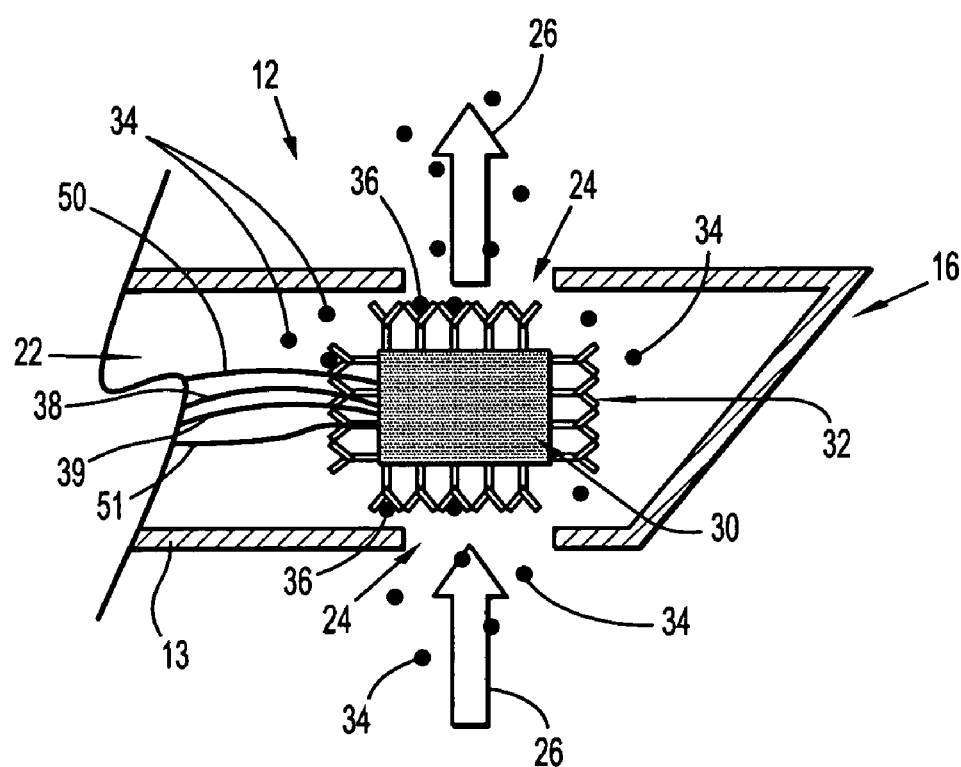
FIG. 2 is a cross-sectional view of the entry end of the probe of the blood analyzer illustrating the biosensor within the probe.

Referring now to FIGS. 1-2, the blood analyzer 10 in accordance with the principles of the present disclosure is illustrated. Generally blood analyzer 10 includes an access member or a probe 12 and a monitor 20 in electrical communication with the probe 12. The probe 12 has a proximal end 14 and a distal end 16. The probe 12 may be any tubular structure (e.g., a catheter or a cannula) having a housing 13 and a lumen 22 defined therein and one or more ports 24 at the distal end 16 thereof adapted to provide fluid access to the lumen 22. The distal end 16 of the probe 12 is inserted into a blood vessel "V" to allow for the blood to flow into the lumen as illustrated by directional arrows 26. It is envisioned that the distal end 16 may be configured for penetration and insertion into the blood vessel "V." Alternatively, a tissue-penetrating device may be utilized to create an orifice in the blood vessel "V" into which the probe 12 is later inserted. The blood flows into and through the lumen 22 through the ports 24.

Probe 12 includes an acoustic biosensor 30 disposed within the lumen 22 which is in fluid communication with the blood flowing through the blood vessel "V." This allows for the blood analyzer 10 to continuously monitor the blood stream for analyte 34 of interest. The acoustic biosensor 30 may be a piezoelectric material (e.g., quartz crystal) and includes a capture agent 32 disposed on the surface thereof. The capture agent 32 may be, for example, specific antibodies adapted to bind to an analyte 34 of interest. Analytes of interest include cardiac troponin, myoglobin, creatinine kinase, creatine kinase isozyme MB, albumin, myeloperoxidase, C-reactive protein, glucose and the like. The capture agent 32 may be bound to the surface of the acoustic biosensor 30 using any number of conventional deposition techniques, such as covalent bonding, physical absorption, cross-linking to a suitable carrier matrix. During operation, the biosensor 30 is in fluid communication with the blood. If analyte 34 is present in the blood, the analyte 34 binds to the capture agent 32 to form a bound complex 36. As the capture agent 32 continuously binds to the analyte 34 to form the complex 36, the effective mass of the biosensor 30 increases. Thus, the acoustic biosensor 30 detects the amount of the analyte 34 by measuring changes in the mass. The mass change is measured by measuring changes in electrical and mechanical properties of the biosensor 30. Passing an electrical current through the biosensor 30 and measuring changes in the electrical current or the electrical potential allows for measuring changes in effective mass of the biosensor 30. The change in mass of the biosensor 30 may also be determined by exciting the biosensor 30 and measuring the change in resonant frequency of the biosensor 30.

The biosensor 30 is coupled to the monitor 20 via two or more wires, such as an excitation wires 38, 50 and a detection wire 39, 51. The probe 12 at its proximal end 14 includes a cable 18 which encloses the wires 38, 39, 50, 51. The monitor 20 includes an oscillator, a detector, input controls, and a display (not explicitly shown). The oscillator and the detector are coupled to the biosensor 30 via the excitation wires 38, 50 and the detection wires 39, 51 respectively. The wires 38, 39, 50, 51 include one or more electrodes in electrical communication with the biosensor 30. The oscillator provides an electrical signal to the biosensor 30 which drives the biosensor 30 at the corresponding resonant frequency. The frequency is transmitted along the detection wire 39, 51 to the detector wherein the change in mass of the biosensor 30 is determined.

Mass calculation is performed by using a Sauerbey relationship wherein a change in the measured frequency of the piezoelectric crystal is expressed as a change in mass thereof. The resulting increase in the mass produces a decrease in the resonant frequency of the biosensor 30. The detector includes programmable instructions (e.g., algorithm) adapted to calculate the change in mass of the biosensor 30 as a function of the change in the measured frequency. The instructions may include the Sauerbey formula as well as any required constants describing the piezoelectric material. Such constants include piezoelectrically active area, density and shear modulus of the crystal.

An increase in mass of the biosensor 30 signifies that the analyte 34 has been captured by the capture agent 32 to form the complex 36. The data describing the calculated mass changes is formatted for output on the display. This step may include displaying that the analyte 34 is present in the blood stream (e.g., displaying text "analyte detected."). It is further contemplated that the detector is configured to calculate a derivative of the change in mass. The rate of change in the resonant frequency correlates to the changes in the mass of the analyte in the blood stream. This relationship allows for determination of concentration and change in concentration of the analyte 34. In particular, the rate of increase of the mass of the biosensor 30 allows for determination of the concentration of the analyte 34. Taking a second time derivative of the measured mass allows for calculation of the rate of change in the concentration of the analyte 34. It is within the purview of those skilled in the art to provide programmable instructions to the detector to enable calculation of derivatives. The data relating to the concentration of the analyte 34 in the bloodstream allows for a more detailed analysis of the test results. In particular, as opposed to simply outputting whether the analyte 34 is present in the bloodstream, knowing the concentration of the analyte 34 and the rate at which the analyte 34 is being generated provides health professionals with a tool to determine the severity of the condition (e.g., myocardial infarction). The detected concentration or the change in concentration of the analyte 34 may be outputted as grams per liter of blood (e.g., μg/L).

The blood analyzer 10 allows for continuous monitoring of the analyte 34. During operation, the probe 12 is inserted into the blood vessel such that the biosensor 30 is in fluid communication with the blood and the monitor 20 is calibrated. Calibration includes acquiring the fundamental frequency of the biosensor 30 which corresponds to zero net mass gain, such that any subsequent mass gain detected by the monitor 20 is indicative of the presence of the analyte 34.

The oscillator and the detector operate in sequence, such that when the oscillator transmits an excitation pulse to the biosensor 30 the detector is activated to receive the frequency signal. It is contemplated that the monitor 20 interrogates the biosensor 30 on a periodic basis (e.g., every minute) wherein the oscillator and the detectors are activated for relatively short periods of time with pauses between interrogations, therefore approximating a continuous measurement. Those skilled in the art will understand that various proteins indicative of specific biological conditions are generated at different rates, therefore the length of interrogation period may be adjusted based on the type of analyte.

The biosensor 30 ceases to function when all of the antibodies are bound to the analyte 34 and no more analyte 34 can be bound thereto. Therefore, the duration of the functionality of the biosensor 30 varies with the concentration of the analyte 34 in the patient's blood. It is preferable that the duration of operation about 8 hours with patients having low analyte concentration to ensure proper detection.

Figure 3:
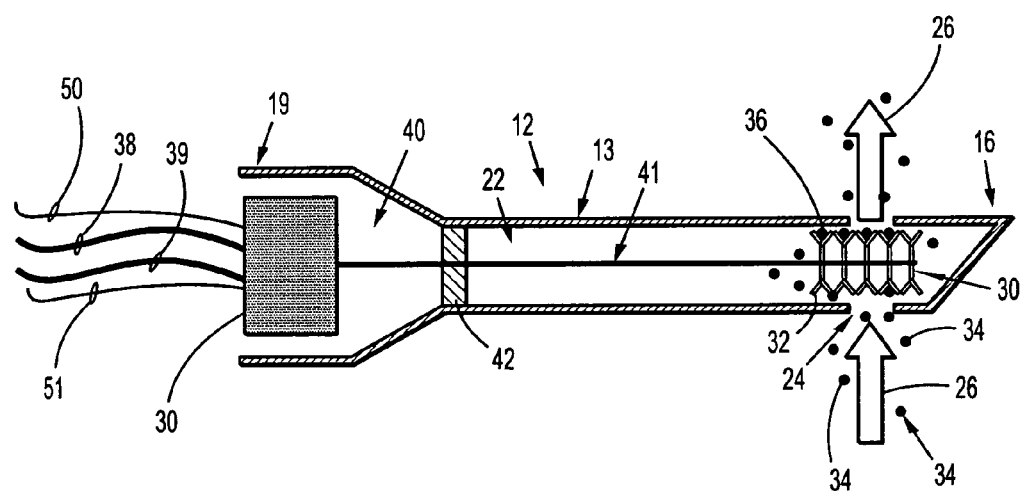
FIG. 3 is a cross-sectional view of another embodiment of the probe according to the present disclosure.

FIG. 3 shows another embodiment of the probe 12 which includes the biosensor 30 disposed within a chamber 40 of the lumen 22. The biosensor 30 includes an extension member 41 having the capture agents 32 disposed at a distal end thereof.

During operation, the blood flows into the lumen 22 through the ports 24 carrying the analyte 34 which then binds to the capture agents 32. The biosensor 30 is excited by the monitor 20 in the manner discussed above to determine the change in mass. Since the extension member 41 is coupled to the biosensor 30 the changes in mass caused by the binding of the analyte 34 to form the complex 36 are detected by the monitor 20.

The extension member 41 may be a cantilever beam manufactured from a medical grade material (e.g., stainless steel) or a suture filament. Optionally, the chamber 40 may be separated from the rest of the lumen 22 via a seal 42. The seal 42 may be formed from hydrogel and other materials which do not affect acoustic properties of the biosensor 30. This prevents the blood from flowing into the chamber 40 and contacting the biosensor 30 further isolating the biosensor 30.

The biosensor 30 of the embodiment shown in FIG. 2, must be removed after the blood analysis is complete since the biosensor 30 includes bound complexes 36 on the surface thereof. In contrast, the biosensor 30 of the embodiment shown in FIG. 3 may be reused. By depositing the capture agents 32 on the extension member 41, the analytes 34 do not bind to the surface of the biosensor 30. Consequently, the biosensor 30 may be reused and the extension member 41 may be replaced after the analysis is complete.

It is also envisioned that the biosensor 30 may be disposed within the venous system using a variety of other types of medical devices adapted for insertion into blood vessels which provide for blood flow therethrough. Contemplated devices include but are not limited to shunts and stents.

Figure 4:
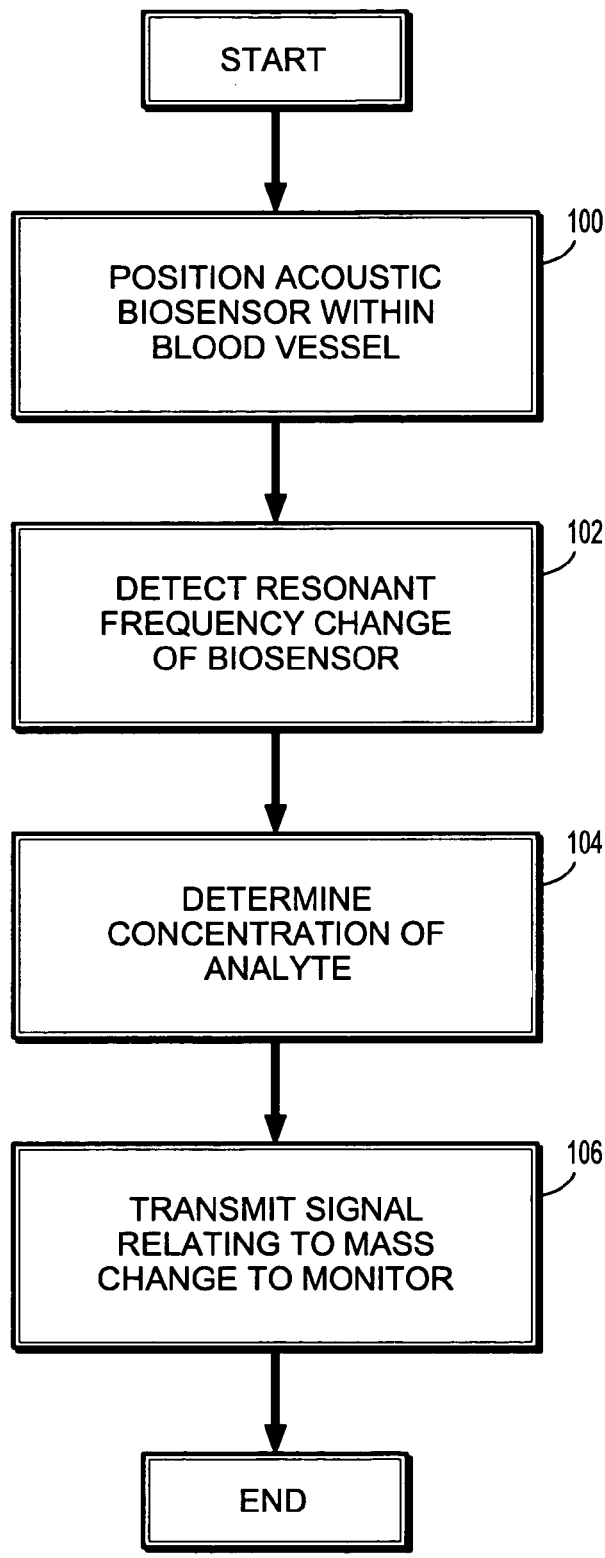
FIG. 4 is a flow diagram of a method for performing a blood assay according to the present disclosure.

A method for performing a blood assay is illustrated in FIG. 4. In step 100, the biosensor 30 is positioned in fluid communication with the blood vessel "V." This is accomplished by positioning the biosensor 30 within an access member (e.g., probe 12) which is then inserted into the blood vessel. As discussed above, when the probe 12 is inserted into the blood vessel, the blood flows into the lumen 22 thereby positioning the biosensor 30 in fluid communication with the blood.

In step 102, the biosensor 30 is excited by the oscillator, which generates a mechanical wave form in the biosensor 30 at the resonant frequency thereof. The resonant frequency of the biosensor 30 is monitored by the detector which detects changes in resonant frequency as a result of the increase in effective mass of the biosensor 30. The increase in effective mass is attributed to the binding of the analyte 34 to the capture agent 32 disposed on the surface of the biosensor 30.

In step 104, the concentration and change in concentration of the analyte 34 is determined by the detector. The detector calculates the concentration by measuring the change in the resonant frequency. The change in concentration of the analyte 34 is determined by calculating the rate of increase of the effective mass of the biosensor 30. The rate of change of concentration of the analyte 34 is calculated by taking a second time derivative of the effective mass of the biosensor 30.

In step 106, the detector transmits the signal relating to the mass change (e.g., change in resonant frequency) to the display of the monitor 20 to provide a clinician with real time analysis of the level of the analyte 34. The signal may include, but is not limited to, an indicator that analyte 34 is present, an indicator of the concentration of the analyte 34, and an indicator of the change in concentration of the analyte 34. The clinician then compares the concentration of the analyte to a first predetermined clinical threshold to determine if a particular treatment is warranted.

Further, the monitor 20 is also adapted to display the rate of change in the analyte concentration. The clinician compares the rate of change in analyte concentration to a second predetermined clinical threshold to determine if a particular treatment is warranted. The monitor 20 may optionally include automatic alarms to alert the clinician that the analyte concentration has exceeded one or more threshold values.

While several embodiments of the disclosure have been shown in the drawings and/or discussed herein, it is not intended that the disclosure be limited thereto, as it is intended that the disclosure be as broad in scope as the art will allow and that the specification be read likewise. For example, it is envisioned that the biosensor and/or monitor could evaluate or perform an assay on other body fluid, tissues, enzymes etc. Therefore, the above description should not be construed as limiting, but merely as exemplifications of particular embodiments. Those skilled in the art will envision other modifications within the scope and spirit of the claims appended hereto.

What is claimed is:

1. A method for performing a tissue assay, comprising the steps of:
    positioning an acoustic biosensor including an extension member in fluid communication with tissue of the patient whereby the tissue contacts the extension member, the extension member having at least one material adapted to bind to an analyte;
    detecting a change in at least one of an electrical and mechanical property of the biosensor indicative of a mass change resulting from binding of the at least one material with the analyte; and
    transmitting a real time signal representative of a mass change to a display module to provide real time analysis by a clinician.

2. A method for performing a blood assay, comprising the steps of:
    positioning an acoustic biosensor including an extension member in fluid communication with a blood vessel of the patient whereby blood from the blood vessel contacts the extension member, the extension member having at least one material adapted to bind to an analyte;
    detecting a change in at least one of an electrical and mechanical property of the biosensor indicative of a mass change resulting from binding of the at least one material with the analyte; and
    transmitting a real time signal representative of a mass change to a display module to provide real time analysis by a clinician.

3. The method according to claim 2 wherein the acoustic biosensor comprises a piezoelectric crystal and wherein, during the step of detecting, the analyte attaches to the at least one material to increase an effective mass of the extension member.

4. The method according to claim 3 wherein the at least one material is adapted to attach to the analyte to increase the effective mass of the extension member, the analyte being selected from the group consisting of cardiac troponin, myoglobin, creatinine kinase, creatine kinase isozyme MB, albumin, myeloperoxidase, C-reactive protein and glucose.

5. The method according to claim 2 wherein the step of positioning includes introducing the extension member within the lumen of the blood vessel.

6. The method according to claim 5 including the step of accessing the blood vessel with an access member having at least one port to permit passage of the blood therethrough whereby the extension member is disposed within a distal end of the access member.

7. The method according to claim 2 including the step of accessing the blood vessel with an access member and withdrawing the blood through the access member to contact the extension member remotely from the blood vessel.

8. The method according to claim 7 including the step of returning the blood to the blood vessel.

9. The method according to claim 2, wherein the at least one electrical property of the biosensor is selected from the group consisting of an electrical current and an electrical potential.

10. The method according to claim 2, wherein the at least one mechanical property of the biosensor is a resonant frequency of the biosensor.

11. The method according to claim 10, including the step of calculating the rate of the resonant frequency change.

12. The method according to claim 10, including the step of calculating at least one time derivative of the resonant frequency change to determine concentration of the analyte within the blood.

13. The method according to claim 2 wherein the step of detecting is performed substantially in real time.

14. A medical analyzer to assay blood for an analyte, which comprises:
   an acoustic biosensor including an extension member adapted to be in fluid communication with a blood vessel whereby blood from the blood vessel contacts the extension member, the extension member having at least one material adapted to bind to an analyte of the blood;
   an oscillator for generating a mechanical wave form in the biosensor; and
   a detector adapted to detect a change in resonant frequency of the mechanical wave form indicative of a mass change resulting from the binding of the at least one material of the extension member with the analyte of the blood and to generate a real time signal representative of the mass change of the biosensor to provide real time analysis by a clinician.

15. The medical analyzer according to claim 14, including a monitor adapted to receive the real time signal transmitted by the transmitter and provide a visual display corresponding to the mass change.

16. The medical analyzer according to claim 15, including a controller for performing calculations pertaining to the mass change of the extension member.

17. The medical analyzer according to claim 16, wherein the controller includes programming to calculate a rate of the mass change of the extension member, the monitor being adapted to provide a visual display corresponding to the rate of the mass change.

18. The medical analyzer according to claim 17, wherein the controller includes programming to calculate at least one time derivative of the rate of the mass change of the extension member corresponding to concentration level of the analyte, the monitor being adapted to provide a visual display corresponding to the concentration level.

19. The medical analyzer according to claim 14, including an access member for accessing the blood vessel and having the extension member disposed within a lumen thereof, whereby blood passes through the lumen to contact the extension member.

20. The medical analyzer according to claim 19, wherein the access member includes a distal end adapted to penetrate the blood vessel to thereby be at least partially positioned therein, the extension member being disposed within the distal end of the access member.

21. The medical analyzer according to claim 20, wherein the distal end includes an entry port to permit entry of the blood within the lumen of the access member for contacting the extension member and an exit port for returning the blood to the blood vessel.

22. The medical analyzer according to claim 14, wherein the at least one material is adapted to bind to cardiac troponin.

23. A medical analyzer to assay blood for an analyte, which comprises:
   an acoustic biosensor including an extension member adapted to be in fluid communication with a blood vessel whereby blood from the blood vessel contacts the extension member, the extension member having at least one material adapted to bind to an analyte of the blood, the biosensor being adapted to transmit a mass change resulting from the binding of the at least one material of the extension member with the analyte of the blood in response to a change in at least one of an electrical and mechanical property of the biosensor.

24. The medical analyzer according to claim 23, wherein the at least one electrical property of the biosensor is selected from the group consisting of an electrical current and an electrical potential.

25. The medical analyzer according to claim 23, wherein the at least one mechanical property of the biosensor is a resonant frequency of the biosensor.

* * * * *